United States Patent
Welz-Biermann et al.

(10) Patent No.: US 7,632,969 B2
(45) Date of Patent: Dec. 15, 2009

(54) PROCESS FOR THE PREPARATION OF PERFLUOROALKYLPHOSPHINES AND THE USE THEREOF AS PERFLUOROALKYLATING REAGENTS

(75) Inventors: Urs Welz-Biermann, Heppenheim (DE); Nikolai Ignatyev, Duisburg (DE); Michael Weiden, Darmstadt (DE); Michael Schmidt, Seeheim-Jugenheim (DE); Udo Heider, Winchester (GB); Alexej Miller, Duisburg (DE); Helge Willner, Muehlheim/Ruhr (DE); Peter Sartori, Utting (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/738,985

(22) Filed: Apr. 23, 2007

(65) Prior Publication Data

US 2007/0191637 A1 Aug. 16, 2007

Related U.S. Application Data

(62) Division of application No. 10/511,554, filed as application No. PCT/EP03/02739 on Mar. 17, 2003, now Pat. No. 7,208,626.

(30) Foreign Application Priority Data

Apr. 18, 2002 (DE) ................. 102 16 998

(51) Int. Cl.
*C07C 9/02* (2006.01)
(52) U.S. Cl. .................. 562/808; 562/818; 568/8
(58) Field of Classification Search ................. 562/808, 562/818; 568/8
See application file for complete search history.

(56) References Cited

U.S. PATENT DOCUMENTS 4,701,569 A 10/1987 Francese et al.
6,096,926 A 8/2000 Roques et al.

FOREIGN PATENT DOCUMENTS

FR 2827285 1/2003

OTHER PUBLICATIONS

Gilje et al., Preparation and nuclear magnetic resonance parameters of perfluoroalkyl-substituted phosphorus(V) hydrides, Journal of the Chemical Society, Chemical Communications, 1973, 813-814.*
Kampa et al., The synthesis of tris(perfluoroalkyl)phosphanes, Angewandte Chemie, International Edition in English (1995), 34(11), 1241-1244.*
Mahmood, et al., Comparative study of tris(trifluoromethyl)phosphine oxide, tris(nonafluorobutyl) phosphine oxide and fluorobis(nonafluorobutyl)phosphine oxide with ammonia and amines, Inorg. Chem, 1988; 27(17); 2913-2916.
Gilje, et al., Preparation and nuclear magnetic resonance parameters of perfluoroalkyl-substituted phosphorus(V) hydrides, Journal of the Chemical Society, Chemical Communications, 1973, 813-814.
Kampa, et al., The Synthesis of Tris(perfluoroalkyl)phosphanes, Angewandte Chemie, 1995, 34 (11), 1241-1244.

* cited by examiner

*Primary Examiner*—Daniel M Sullivan
*Assistant Examiner*—Chukwuma O Nwaonicha
(74) *Attorney, Agent, or Firm*—Millen, White, Zelano, Branigan, P.C.

(57) ABSTRACT

The present invention relates to a process for the preparation of perfluoroalkylphosphines comprising at least the reaction of at least one fluoro(perfluoroalkyl)phosphorane with at least one hydride ion donor, and to the use of tris(perfluoroalkyl)phosphines as perfluoroalkylating reagents.

12 Claims, No Drawings

PROCESS FOR THE PREPARATION OF PERFLUOROALKYLPHOSPHINES AND THE USE THEREOF AS PERFLUOROALKYLATING REAGENTS

RELATED APPLICATIONS

This application is a divisional of U.S. patent application Ser. No. 10/511,554, filed Oct. 18, 2004, now U.S. Pat. No. 7,208,626 which is a §371 of PCT/EP03/2739, filed Mar. 17, 2003.

The present invention relates to a process for the preparation of perfluoroalkylphosphines comprising at least the reaction of at least one fluoro(perfluoroalkyl)phosphorane with at least one hydride ion donor, and to the use of perfluoroalkylphosphines as perfluoroalkylating reagents.

Perfluoroalkylphosphines are known per se. Some compounds are obtained by the process described in the literature by reduction of corresponding difluorotris(perfluoroalkyl) phosphoranes using $P[Si(CH_3)_3]_3$ (J. J. Kampa et al., Angew. Chem., 107, No. 11 (1995), pages 1334-1337). Disadvantageous in this process is, in particular, the very low yield of the perfluoroalkylphosphines and the relatively complex preparation of the reducing agent $P[Si(CH_3)_3]_3$.

The object of the present invention was therefore to provide a process which enables the simple and inexpensive preparation of perfluoroalkylphosphines in good yields. The perfluoroalkylphosphines should preferably be obtained in high purity.

This object has been achieved by the process according to the invention for the preparation of perfluoroalkylphosphines which comprises at least the reaction of at least one fluoro (perfluoroalkyl)phosphorane with at least one hydride ion donor.

Fluoro(perfluoroalkyl)phosphoranes can be prepared by conventional methods known to the person skilled in the art.

These compounds are preferably prepared by electrochemical fluorination of suitable starting compounds, as described in V. Ya. Semenii et al., Zh. Obshch. Khim., 55, No. 12 (1985), pages 2716-2720; N. Igantiev, P. Sartori, J. of Fluorine Chem., 103 (2000), pages 57-61 and WO 00/21969. The corresponding descriptions are incorporated herein by way of reference and are regarded as part of the disclosure.

In accordance with the invention, one or more hydride ion donors, i.e. compounds which are capable of releasing one or more hydride ions (H⁻), can in each case be used individually or in combination, the use of in each case only one hydride ion donor being preferred.

The hydride ion donor is preferably selected from the group consisting of hydrosilanes, alkylhydrosilanes, metal hydrides, borohydrides and hydro-borates.

If the hydride ion donor used in the process according to the invention is an alkylhydrosilane, this is preferably triethylsilane or tripropylsilane.

If the hydride ion donor used in the process according to the invention is a borohydride, this is preferably sodium borohydride.

In a preferred embodiment of the process according to the invention, at least one fluoro(perfluoroalkyl)phosphorane compound of the general formula I $$(C_nF_{2n+1})_mPF_{5-m} \qquad \text{I}$$

where $1 \leq n \leq 8$, preferably $1 \leq n \leq 4$, and m is in each case 1, 2 or 3, is reacted in accordance with the process according to the invention.

Particularly preferred fluoro(perfluoroalkyl)phosphorane compounds can be selected from the group consisting of difluorotris(pentafluoroethyl)phosphorane, difluorotris(n-nonafluorobutyl)phosphoranes, difluorotris(n-heptafluoropropyl)phosphoranes and trifluorobis(n-nonafluorobutyl) phosphorane.

The reaction of at least one fluoro(perfluoroalkyl)phosphorane compound can be carried out either in a suitable reaction medium or without the presence of a reaction medium. The reaction by the process according to the invention is preferably carried out without a reaction medium since the environmental balance of the process is thereby improved and the costs reduced.

The hydride ion donors used in the process according to the invention are preferably employed in excess, in each case based on the amount of fluoro(perfluoroalkyl)phosphorane employed, in order to ensure complete conversion to the desired perfluoroalkylphosphines. The hydride ion donors can likewise preferably be employed in an equimolar amount, in each case based on the amount of fluoro(perfluoroalkyl) phosphorane employed.

In the process according to the invention, the temperature during the reaction and the duration of the reaction can be varied over a broad range, for example depending on one another and depending on the fluoro(perfluoroalkyl)phosphorane employed and the batch sizes selected in each case. The optimum choice of parameters in each case can be determined by the person skilled in the ad through simple preliminary experiments.

In a preferred embodiment of the process according to the invention, refluxing is carried out during the reaction of the fluoro(perfluoroalkyl)phosphorane.

The duration of the reaction is preferably from 0.5 to 20 hours. The duration is particularly preferably from 3 to 15 hours if triethylsilane is used as hydride ion donor, and particularly preferably from 1 to 3 hours for sodium borohydride.

The preparation of one or more perfluoroalkylphosphines by the process according to the invention can be followed, if necessary, by purification of these compounds by conventional methods known to the person skilled in the art.

In a preferred embodiment of the process according to the invention, the perfluoroalkylphosphines prepared can be purified and, if desired, isolated by single or multiple distillation, if desired under reduced pressure and/or if desired under an inert-gas atmosphere.

The process according to the invention for the preparation of perfluoroalkylphosphines enables the inexpensive preparation of these compounds in high yield and in high purity. It is furthermore distinguished by the fact that the hydride ion donors used are commercially available, inexpensive compounds which can be handled without problems even on a large industrial scale. The fluoro(perfluoroalkyl)phosphoranes employed as starting compounds can likewise be prepared inexpensively by electrochemical fluorination.

It is furthermore advantageous that the process according to the invention can be carried out without a solvent, which further reduces the preparation costs of the perfluoroalkylphosphines and improves the environmental balance of the process according to the invention.

Surprisingly, it has also been found that tris(perfluoroalkyl) phosphines are suitable for the perfluoroalkylation of chemical substrates.

Perfluoroalkylation is an important process for the preparation of fluorine-containing compounds, in particular organofluorine compounds. The perfluoroalkylating reagents usually employed are perfluoroalkyl halides, in particular perfluoroalkyl iodides, which function as a source of perfluoroalkyl free radicals ("Organofluorine Chemistry. Principles and Commercial Applications." Edited by R. E. Banks, Plenum Press, New York 1994; G. G. Furin, "Some new aspects in the application of perfluoroalkyl halides in the synthesis of fluorine-containing organic compounds" (Review), Russ. Chem. Rev. (English Translation), 69, No. 6 (2000), pages 491-522; N. O. Brace, "Syntheses with perfluoroalkyl iodides. A review, Part III.", J. of Fluorine Chem., 108 (2001), pages 147-175; N. O. Brace, "Syntheses with perfluoroalkyl iodides. Part II.", J. of Fluorine Chem. 96 (1999), pages 101-127; N. O. Brace, "Syntheses with perfluoroalkyl radicals from perfluoroalkyl iodides. A rapid survey of synthetic possibilities with emphasis on practical applications, Part one: alkenes, alkynes and allylic compounds", J. of Fluorine Chem., 96 (1999), pages 1-25; V. N. Boiko, "Ion-radical perfluoroalkylation. Part II.", J. of Fluorine Chem., 69 (1994), pages 207-212).

In addition, perfluoroalkyl halides are employed for the preparation of organometallic compounds containing perfluoroalkyl, in particular trifluoromethyl, groups, which can themselves be employed for introducing perfluoroalkyl groups into organic molecules (D. J. Burton, "Fluorinated organometallics: perfluoroalkyl and functionalised perfluoroalkyl organometallic reagents in organic synthesis", Tetrahedron, 48, No. 2 (1992), pages 189-275).

Furthermore, the reagent $TMSCF_3$ has been developed for nucleophilic trifluoromethylation (G. K. Surya Prakash, "Nucleophilic trifluoromethylation tamed", J. of Fluorine Chem., 112 (2001), pages 123-131). This nucleophilic perfluoroalkylation process has been extended to further organic and inorganic substrates through the reaction of long-chain perfluoroalkyl iodides with tetrakis(dimethylamino)ethylene in the presence of chlorotrimethylsilane (V. A. Petrov, Tetrahedron Letters, 42 (2001), pages 3267-3269).

However, the above-mentioned perfluoroalkylation processes have the disadvantage that the corresponding perfluoroalkyl halides are either very expensive or their use is only allowed with very great restrictions in accordance with the Montreal Protocol, as, for example, in the case of the compound $CF_3Br$.

These disadvantages have resulted in the development of novel perfluoroalkylating reagents, as described in J. R. Desmurs et al., 12th European Symposium on Fluorine Chemistry, Berlin, Germany, 1998, Abstracts A23 and A24. However, these reagents can only be prepared using $CF_3H$, a highly volatile compound which is difficult to handle. Furthermore, other stable perfluoroalkylating reagents have been developed for nucleophilic trifluoromethylation, the synthesis of these reagents starting from the methyl hemiketal of fluoral, which first has to be prepared in a relatively complex process. In addition, the use of these reagents is restricted to trifluoromethylation (G. Blond et al., Tetrahedron Letters, 42 (2001), pages 2437-2475; T. Billard et al., Eur. J. Org. Chem., 2001, pages 1467-1471; T. Billard et al. Tetrahedron Letters, 41 (2000), pages 8777-8780; G. Blond et al., J. Org. Chem., 66, No. 14 (2001), pages 4826-4830).

The present invention therefore furthermore relates to the use of at least one tris(perfluoroalkyl)phosphine for the perfluoroalkylation of chemical substrates.

For the perfluoroalkylation of chemical substrates using perfluoroalkylphosphines, it is necessary to treat the substrate to be perfluoroalkylated with at least one base either before or during the reaction with the respective perfluoroalkylphosphine. The perfluoroalkylation of the chemical substrate using at least one perfluoroalkylphosphine is preferably carried out in the presence of at least one base.

Preference is given here to strong bases, such as, for example, potassium tert-butoxide, n-butyllithium and/or a Grignard reagent.

The perfluoroalkylation is preferably carried out in a suitable reaction medium, if necessary dried by conventional methods, such as, for example, cyclic or aliphatic ethers, in particular tetrahydrofuran or diethyl ether.

Suitable chemical substrates are preferably organic compounds, in particular tricoordinated organoboron compounds and organic compounds containing carbonyl groups.

Preferred organoboron compounds employed are tris($C_{1-3}$) alkylborates, particularly preferably trimethyl borate.

Preferred carbonyl group-containing compounds are optionally substituted diaryl ketone compounds, in particular benzophenone.

The perfluoroalkylation of chemical substrates using perfluoroalkylphosphines can preferably be carried out under an inert-gas atmosphere, such as, for example, argon or nitrogen.

The use of tris(perfluoroalkyl)phosphines as perfluoroalkylating reagents is advantageous in particular since these compounds, in contrast to many other perfluoroalkylating reagents, are stable compounds, which enables them to be handled simply and safely.

The NMR spectra were recorded with the aid of a Bruker Avance 300 NMR spectrometer with the following frequencies:

300.1 MHz for $^1H$ 282.4 MHz for $^{19}F$ and 96.3 MHz for $^{11}B$.

The mass spectra were measured using an AMD 604 instrument.

The invention is explained below with reference to examples. These examples serve merely to explain the invention and do not restrict the general inventive idea.

EXAMPLES

Example 1a

Preparation of tris(pentafluoroethyl)phosphine 56.0 g (131.4 mmol) of difluorotris(pentafluoroethyl) phosphorane and 38.0 g (326.8 mmol) of triethylsilane were refluxed with vigorous stirring for 12 hours in an FEP (fluoroethylene polymer) flask at a bath temperature of 110° C. The reaction mixture was subsequently distilled under atmospheric pressure under an inert-gas atmosphere, and 48.0 g of the fraction having a boiling range of 81-85° C. were collected. This fraction was subsequently cooled to −20° C., and the lower phase (desired product) was separated off. 42.2 g of virtually pure tris(pentafluoroethyl)phosphine were obtained, corresponding to a yield of 82.8%, based on the difluorotris(pentafluoroethyl)phosphorane employed.

The resultant product was characterised by means of $^{19}F$-, $^{31}P$- and $^1H$-NMR spectroscopy and by mass spectroscopy:

$^{19}F$ NMR spectrum; δ, ppm: (solvent $CDCl_3$, internal reference $CCl_3F$) −82.4 dt ($CF_3$); −106.5 dq ($CF_2$); $J^2_{P,F}$=49.3 Hz; $J^3_{P,F}$=15.8 Hz; $J^3_{F,F}$=3.1 Hz $^{31}P$ NMR spectrum; δ, ppm: (solvent $CDCl_3$, reference 85% by weight $H_3PO_4$) 13.3 sep of dec The values of the chemical shifts found correspond to the values disclosed in the publication by J. J. Kampa et al., Angew. Chem., 107, No. 11 (1995), pages 1334-1337.

High-resolution mass spectrum: Calculated (M+): 387.949812 Found (M+): 387.949842

Example 1b

Preparation of tris(pentafluoroethyl)phosphine 230.0 g (0.54 mol) of difluorotris(pentafluoroethyl)phosphorane and 41.2 g (1.089 mol) of sodium borohydride were refluxed with vigorous stirring for 3 hours in a glass flask at a bath temperature of about 110° C. The reaction mixture was subsequently distilled under reduced pressure (2 kPa), and two fractions of the product were collected in cold traps at a temperature of −78° C. and −195° C. respectively. For further purification, the combined products from both traps were distilled under atmospheric pressure under an inert-gas atmosphere, with the fraction in the boiling range 85-87° C. being collected. 194.0 g of pure tris(pentafluoroethyl)phosphine were obtained. The yield was 93%, based on the amount of difluorotris(pentafluoroethyl)phosphorane employed. The resultant product was characterised by means of $^{19}$F- and $^{31}$P-NMR spectroscopy. The chemical shifts found correspond to those from Example 1a.

Example 2

Preparation of tris(n-nonafluorobutyl)phosphine 19.7 g (27.13 mmol) of difluorotris(n-nonafluorobutyl)phosphorane and 10.0 g (86.0 mmol) of triethylsilane were refluxed with vigorous stirring for 15 hours in an FEP flask at a bath temperature of about 140° C. The reaction mixture was subsequently distilled under reduced pressure (1.73 kPa), and the fraction having a boiling point of 87° C. was collected. 15.0 g of the clear, colourless liquid of tris(n-nonafluorobutyl)phosphine were obtained. The yield was 80.3%, based on the amount of difluorotris(n-nonafluorobutyl)phosphorane employed.

The resultant product was characterised by means of $^{19}$F- and $^{31}$P-NMR spectroscopy and by elemental analysis:

$^{19}$F NMR spectrum; δ, ppm: (solvent CDCl$_3$, internal reference CCl$_3$F) −81.4 t (CF$_3$); −102.2 dm (CF$_2$); −118.9 dm (CF$_2$); −126.3 m (CF$_2$) $J^2_{P,F}$=37.7 Hz; $J^3_{P,F}$=35.2 Hz; $J^4_{F,F}$=9.6 Hz $^{31}$P NMR spectrum; δ, ppm: (solvent CDCl$_3$, reference 85% by weight H$_3$PO$_4$) 23.3 m The values of the chemical shifts found correspond to the values disclosed in the publication by J. J. Kampa et al., Angew. Chem., 107, No. 11 (1995), pages 1334-1337.

Example 3

Preparation of bis(n-nonafluorobutyl)phosphine 4.6 g (8.7 mmol) of trifluorobis(n-nonafluorobutyl)phosphorane and 4.32 g (27.3 mmol) of tripropylsilane were refluxed with vigorous stirring for 3 hours in an FEP flask at a bath temperature of about 70° C. The reaction mixture was subsequently distilled under atmospheric pressure and under an inert-gas atmosphere, and the fraction in the boiling range 130-135° C. was collected. 3.0 g of the clear, colourless liquid of bis(n-nonafluoro-butyl)phosphine were obtained. The yield was 73.3%, based on the amount of trifluorobis(n-nonafluorobutyl)phosphorane employed.

The resultant product was characterised by means of $^{19}$F- and $^{31}$P-NMR spectroscopy. The spectra were measured for the pure liquid using an FEP tube with an acetonitrile-D$_3$ film as external lock and CCl$_3$F or 85% H$_3$PO$_4$ in D$_2$O as external reference.

$^{19}$F NMR spectrum; δ, ppm: −81.6 m (CF$_3$); −120.2 m (CF$_2$); −121.1 m (CF$_2$); −126.0 m (CF$_2$)

$^{31}$P NMR spectrum; δ, ppm: 140.0 dm; $J^1_{P,H}$=1025 Hz

Example 4

Perfluoroalkylation of benzophenone 5.81 g (14.97 mmol) of tris(pentafluoroethyl)phosphine were added under an inert-gas atmosphere to a solution of 1.68 g (14.97 mmol) of potassium tert-butoxide and 2.72 g (14.93 mmol) of benzophenone in 20 cm$^3$ of dried tetrahydrofuran with cooling using a water bath at such a rate that the temperature of the reaction mixture was about 20° C. The reaction mixture was subsequently stirred for a further hour at room temperature, 20 cm$^3$ of a 0.1 N solution of HCl were added, and the mixture was extracted twice with 75 cm$^3$ of diethyl ether each time. The combined extracts were washed three times with 20 cm$^3$ of water each time and dried over anhydrous magnesium sulfate. The solvent was subsequently distilled off, and the desired product was crystallised from n-hexane, giving 2.8 g of 2,2,3,3,3-pentafluoro-1,1-diphenyl-propan-1-ol having a melting point in the range 82-83° C.

The yield was 62%, based on the amount of benzophenone employed.

The resultant product was characterised by means of $^{19}$F- and $^1$H-NMR spectroscopy and by high-resolution mass spectroscopy and elemental analysis:

$^{19}$F NMR spectrum; δ, ppm: (solvent CDCl$_3$, internal reference CCl$_3$F) −77.6 s (CF$_3$); −116.9 m (CF$_2$)

$^1$H-NMR spectrum; δ, ppm: (solvent CDCl$_3$, reference TMS) 7.53-7.67 m (2H), 7.30-7.47 m (3H), 2.85 br.s (OH)

The melting point and the chemical shifts found correspond to the values disclosed in the publication by L. S. Chen et al., J. of Fluorine Chem., 20 (1982), pages 341-348.

High-resolution mass spectrum: Calculated (M+): 302.073006 Found (M+): 302.073115

Elemental analysis: Found; C, 59.67%; H, 3.62%. Calculated for (C$_6$H$_5$)$_2$C(OH)C$_2$F$_5$: C, 59.61%; H, 3.67%.

Example 5

Potassium pentafluoroethyltrifluoroborate
(C$_2$F$_5$)BF$_3$K a)

9.78 g (25.21 mmol) of tris(pentafluoroethyl)phosphine were slowly added under an inert-gas atmosphere to a stirred solution of 30 mmol of n-butyllithium (15 cm$^3$ of a 2 M solution in cyclohexane) in 70 cm$^3$ of dried diethyl ether with cooling at such a rate that the temperature of the reaction mixture was about −60° C. The reaction mixture was subsequently stirred for a further 30 minutes at −55° C., and a solution of 3.31 g (31.85 mmol) of trimethyl borate (CH$_3$O)$_3$B in 5 cm$^3$ of dried diethyl ether was added.

The resultant reaction mixture was brought to room temperature, 30 cm$^3$ of hydrofluoric acid (48% aqueous solution) were added, and the mixture was subsequently stirred at room temperature for a further 10 hours. 10.0 g (128 mmol) of potassium hydrogendifluoride were subsequently added, and the mixture was stirred at room temperature for a further 10 hours. The organic phase was separated off, neutralised by stirring over solid potassium carbonate and dried using anhydrous magnesium sulfate. The solvent was subsequently distilled off, and the resultant residue was dissolved in the smallest possible amount of tetrahydrofuran. Addition of chloroform then caused a solid to precipitate, which was filtered off and dried, giving 3.30 g of potassium pentafluoroethyltrifluoroborate in the form of a white solid. The yield was 58%, based on the tris(pentafluoroethyl)phosphine employed.

The resultant product was characterised by means of $^{11}$B- and $^{19}$F-NMR spectroscopy and by elemental analysis:

$^{11}$B-NMR spectrum; δ, ppm: (solvent acetone-D6, external reference BF$_3$O(C$_2$H$_6$)$_2$): 0.2 tq; $J^1_{B,F}$=41.0 Hz; $J^2_{B,F}$=20.0 Hz $^{19}$F NMR spectrum; δ, ppm: (solvent acetone-D6, internal reference CCl$_3$F) −83.3 q (CF$_3$); −136.2 q, (CF$_2$); −153.5 q (BF$_3$); $J^1_{B,F}$=41.2 Hz; $J^2_{BF}$=19.9 Hz; $J^4_{F,F}$=4.9 Hz.

Elemental analysis: Found: C, 10.56%. Calculated (for (C$_2$F$_5$)BF$_3$K): C, 10.63%.

b)

Potassium pentafluoroethyltrifluoroborate (C$_2$F$_5$)BF$_3$K 20.81 g (53.63 mmol) of tris(pentafluoroethyl)phosphine were slowly added under an inert-gas atmosphere to a stirred solution of 60 mmol of methylmagnesium chloride (20 cm$^3$ of a 3 M solution in tetrahydrofuran) in 100 cm$^3$ of dried tetrahydrofuran with cooling at such a rate that the temperature of the reaction mixture was about −60° C. The reaction mixture was subsequently stirred at −55° C. for a further 30 minutes, and 6.24 g (60.04 mmol) of trimethyl borate (CH$_3$O)$_3$B were added. The resultant reaction mixture was brought to room temperature, 25 cm$^3$ of hydrofluoric acid (48% aqueous solution) were added, and the mixture was subsequently stirred at room temperature for a further 10 hours. 15.0 g (192 mmol) of potassium hydrogendifluoride were subsequently added, and the mixture was stirred at room temperature for a further 10 hours. The organic phase was separated off, neutralised by stirring over solid potassium carbonate and dried using anhydrous magnesium sulfate. The solvent was subsequently distilled off, and the resultant residue was dissolved in the smallest possible amount of tetrahydrofuran. Addition of chloroform then caused a solid to precipitate, which was filtered off and dried, giving 6.30 g of potassium pentafluoroethyltrifluoroborate in the form of a white solid. The yield was 52%, based on the tris(pentafluoroethyl)phosphine employed.

The resultant product was characterised by means of $^{11}$B- and $^{19}$F-NMR spectroscopy. The corresponding signals corresponded to the signals mentioned under 5a.

Example 6

1.925 g (20.53 mmol) of lithium tetrafluoroborate, LiBF$_4$, were dissolved in 10 cm$^3$ of dry dimethyl carbonate. A solution of 4.639 g (20.53 mmol) of potassium pentafluoroethyltrifluoroborate (C$_2$F$_5$)BF$_3$K in 19 cm$^3$ of dry dimethyl carbonate was added at room temperature with stirring. The white precipitate of KBF$_4$ was filtered off. The solvent was removed under reduced pressure (1.3 Pa). The residue (5.525 g, yield: 95%) consisted of lithium pentafluoroethyltrifluoroborate as a complex with dimethyl carbonate (1:1) (C$_2$F$_5$)BF$_3$Li.(CH$_3$O)$_2$CO.

The structure was confirmed by $^{19}$F-, $^{11}$B- and $^1$H-NMR spectra.

$^1$H-NMR spectrum, δ, ppm (solvent: acetonitrile-d$_3$, reference: TMS): 3.74 s, (CH$_3$O)$_2$CO.

$^{11}$B-NMR spectrum, δ, ppm (solvent: acetonitrile-d$_3$, reference: BF$_3$.OEt$_2$ external) −0.1 tq; $J^1_{B,F}$=40.4 Hz; $J^2_{B,F}$=19.9 Hz.

$^{19}$F-NMR spectrum, δ, ppm (solvent: acetonitrile-d$_3$, reference: CCl$_3$F internal) −83.27 q (CF$_3$); −136.14 q (CF$_2$); −154.03 q (BF$_3$); $J^1_{B,F}$=41.2 Hz; $J^2_{B,F}$=19.9 Hz; $J^4_{F,F}$=4.9 Hz.

The invention claimed is:

1. A process for the perfluoroalkylation of a chemical substrate, comprising reacting at least one fluoro(perfluoroalkyl)phosphorane with at least one hydride ion donor to produce a tris(perfluoroalkyl)phosphine, and reacting said tris(perfluoroalkyl)phosphine with said substrate wherein the substrates employed are tris(C$_{1-3}$-alkyl)borates or diarylketones.

2. The process according to claim 1, wherein the fluoro(perfluoroalkyl)phosphorane employed is a compound of formula I $$(C_nF_{2n+1})_mPF_{5-m} \qquad I$$

in which 1≦n≦8, and m is in each case 1, 2 or 3.

3. The process according to claim 1, wherein the fluoro(perfluoroalkyl)phosphorane employed is difluorotris(pentafluoroethyl)phosphorane, difluorotris(n-nonafluorobutyl)phosphorane, trifluorobis(n-nonafluorobutyl)phosphorane or difluorotris(n-heptafluoropropyl)phosphorane.

4. The process according to claim 1, wherein the reaction of fluoro(pentafluoroalkyl)phosphorane and hydride ion is carried out without a reaction medium.

5. The process according to claim 1, wherein the hydride ion donor is a hydrosilane, alkylhydrosilane, metal hydride, borohydride or hydroborate.

6. The process according to claim 5, wherein the alkylhydrosilane is triethylsilane or tripropylsilane.

7. The process according to claim 5, wherein the borohydride is sodium borohydride.

8. The process according to claim 1, wherein the hydride ion donor is employed in an equimolar amount or in excess, in each case based on the amount of fluoro(perfluoroalkyl)phosphorane employed.

9. The process according to claim 1, wherein a reaction mixture of phosphorane and hydride ion is refluxed during reaction.

10. The process according to claim 1, wherein the duration of the reaction phosphorane and hydride ion is from 0.5 to 20 hours.

11. The process according to claim 1, wherein the perfluoroalkylphosphine is purified by distillation, optionally under an inert-gas atmosphere, optionally under reduced pressure.

12. The process according to claim 1, wherein the substrates employed are trimethylborate or benzophenone.

* * * * *